(12) United States Patent
von Weymarn et al.

(10) Patent No.: US 8,338,147 B2
(45) Date of Patent: Dec. 25, 2012

(54) PROCESS FOR PRODUCING D-MANNITOL

(75) Inventors: Niklas von Weymarn, Helsinki (FI); Ulla Airaksinen, Vantaa (FI)

(73) Assignee: zuChem, Inc., Chicago, IL (US)

( * ) Notice: Subject to any disclaimer, the term of this patent is extended or adjusted under 35 U.S.C. 154(b) by 0 days.

(21) Appl. No.: 12/779,666

(22) Filed: May 13, 2010

(65) Prior Publication Data

US 2011/0091949 A1 Apr. 21, 2011

Related U.S. Application Data

(63) Continuation of application No. 10/250,595, filed as application No. PCT/FI01/01127 on Dec. 19, 2001, now abandoned.

(30) Foreign Application Priority Data

Dec. 20, 2000 (FI) ...................................... 20002792

(51) Int. Cl.
*C12P 7/18* (2006.01)
(52) U.S. Cl. ...................... 435/158; 435/170; 435/252.9
(58) Field of Classification Search ........................ None
See application file for complete search history.

(56) References Cited

U.S. PATENT DOCUMENTS 5,635,368 A * 6/1997 Lommi et al. .................. 435/41
6,528,290 B1 * 3/2003 Song et al. ..................... 435/158

FOREIGN PATENT DOCUMENTS

EP 486024 A2 * 5/1992
WO WO 0004181 A1 * 1/2000

OTHER PUBLICATIONS

Soetaert, W et al. The production of mannitol by fermentation. Methods in Biotechnology. 1991. 10: 261-275.*
Korakli, M et al. Production of mannitol by *Lactobacillus sanfranciscensis*. Adv. Food Sci. (CMTL). 2000. 22(1/2): 1-4.*

* cited by examiner

*Primary Examiner* — Allison Ford
*Assistant Examiner* — Susan E Fernandez
(74) *Attorney, Agent, or Firm* — McDonnell Boehnen Hulbert & Berghoff LLP

(57) ABSTRACT

High concentration of free cells of heterofermentative lactic acid bacteria (LAB) in a resting or slowly growing state are used to convert fructose into mannitol. Efficient volumetric mannitol productivities and mannitol yields from fructose are achieved in a process applying cell-recycle, continuous stirred tank reactor and/or circulation techniques with native LAB cells or with LAB cells with inactivated fructokinase gene(s). Mannitol is recovered in high yield and purity with the aid of evaporation and cooling crystallization.

16 Claims, 3 Drawing Sheets

PROCESS FOR PRODUCING D-MANNITOL

This application is a continuation of U.S. patent application Ser. No. 10/250,595 filed on Oct. 30, 2003 now abandoned which is a 371 application of PCT/FI01/01127 filed on Dec. 19, 2001, which in turn claims priority to FI20002792 filed on Dec. 20, 2000.

FIELD OF THE INVENTION

This invention relates to the use of microorganisms, namely lactic acid bacteria (LAB), and concerns particularly a new process for the bioconversion of fructose into mannitol with free, native or fructokinase inactivated cells in a resting or a slowly growing state. The invention also relates to the re-use of the cell biomass for successive bioconversions.

BACKGROUND OF THE INVENTION

D-mannitol is a six-carbon sugar alcohol, which is about half as sweet as sucrose. It is found in small quantities in most fruits and vegetables (Ikawa et al., 1972; Bär, 1985). Mannitol is widely used in various industrial applications. The largest application of mannitol is as a food additive (E421), where it is used e.g. as a sweet tasting bodying and texturing agent (Soetaert at al., 1999). Crystalline mannitol is non-sticky, i.e. it prevents moisture absorption, and is therefore useful as coating material of e.g. chewing gums and pharmaceuticals. In medicine, mannitol is used as osmotic diuretic for intoxication therapy and in surgery, parenteral mannitol solutions are applied to prevent kidney failure (Soetaert at al., 1999). Mannitol is also used in brain surgery to reduce cerebral edema.

At present, commercial production of mannitol is done by catalytic hydrogenation of invert sugar with the co-production of another sugar alcohol, sorbitol. Typically, the hydrogenation of a 50/50-fructose/glucose mixture results in a 30/70 mixture of mannitol and sorbitol (Soetaert at al., 1999). Besides the fact that mannitol is the by-product of the chemical production process and thus liable to supply problems, it is also relatively difficult to separate from sorbitol. In contrast to most sugars and other sugar alcohols mannitol dissolves poorly in water (13% (w/w) at 14° C. (Perry et al., 1997)). Cooling crystallization is therefore commonly used as a separation method for mannitol. However, according to Takemura et al. (1978) the yield of crystalline mannitol in the chemical process is still only approximately 17% (w/w) based on the initial sugar substrates.

In order to improve the total yield of mannitol it would be advantageous to develop a process with mannitol as the main product and with no sorbitol formation. Some alternative processes based on the use of microbes have been suggested in the literature. Yeast, fungi, and LAB especially, are able to effectively produce mannitol without co-formation of sorbitol (Itoh et al. 1992). Among LAB only heterofermentative species are known to convert fructose into mannitol (Pilone et al. 1991; Axelsson, 1993; Soetaert et al. 1999). Species belonging to the genera *Leuconostoc, Oenococcus* and *Lactobacillus* particularly, have been reported to produce mannitol effectively. In addition to mannitol these microbes co-produce lactic and acetic acid, carbon dioxide and ethanol. These by-products are, however, easily separable from mannitol.

Soetaert and co-workers have studied the bioconversion of fructose into mannitol with free cells of *Leuconostoc pseudomesenteroides* ATCC-12291 (Soetaert et al., 1994). Using a fed-batch cultivation protocol they reached a maximum volumetric productivity of 11 g mannitol/L/h and a conversion efficiency of approximately 94 mole-%. Recently, Korakli et al. (2000) reported a 100% conversion efficiency with *Lactobacillus sanfranciscensis* LTH-2590. Other heterofermentative LAB reported to be good producers of mannitol include *Leuconostoc mesenteroides, Oenococcus oeni, Lactobacillus brevis, Lactobacillus buchneri* and *Lactobacillus fermentum* (Pimentel et al., 1994; Salon et al. 1994; Erten, 1998; Soetaert et al. 1999).

In JP62239995, Hideyuki et al. (1987) used free cells of *Lb. brevis*. The volumetric mannitol productivity achieved in batch fermentation was 2.4 g/L/h.

EP0486024 and EP0683152 describe a strain named *Lb.* sp. B001 with volumetric mannitol productivities of 6.4 g/L/h in a free cell batch fermentation (Itoh et al., 1992; Itoh et al., 1995).

More recently, Ojamo et al. (2000) have submitted a patent application for a process for the production of mannitol by immobilized LAB. In this process the average volumetric mannitol productivity and conversion efficiency achieved were approximately 20 g/L/h and 85%, respectively. A low-nutrient medium was used which considerably lowers the production costs. Immobilization also enables the re-use of cell biomass for successive batch fermentations.

These inventions have not yet replaced the conventional hydrogenation process. The free cell bioconversion processes described to date are not entirely suitable for industrial scale production. Volumetric productivities in the range of 20 g/L/h, as achieved with the immobilization process, should however, be adequate for profitable production. In order to further develop the features of the bioconversion alternative, factors such as equipment investment costs, robustness of the process, medium composition (raw material costs), and mannitol yields must be considered and improved. The goal of the present invention is to overcome the prior disadvantages, such as the low productivities obtained with the free cell bioconversion systems and the low mannitol yields characteristic for all available bioconversion systems. Thus, the goal of the present invention is to develop a bioconversion process, which is feasible both technically and economically.

SUMMARY OF THE INVENTION

The present invention is accomplished to overcome the disadvantages mentioned above. The present invention provides a process in which a high concentration of free cells of lactic acid bacteria is applied to the bioconversion of fructose into mannitol. During the bioconversion phase the cells are kept in a resting or a slowly growing state by supplementing to the fructose containing solution only minimal amounts of complex nutrients required for growth. The present invention describes the use of an efficient, high-yield mannitol-producing strain in the process. The strain in question was identified by comparing the mannitol production capabilities of different LAB species kept in a resting or slowly growing state. The present invention also provides an efficient, robust production process with productivities over 20 g mannitol/L/h. In addition, the process concept described here is simple to apply in industrial scale, and because of the low-nutrient medium used in it, the raw material costs are minimized. Furthermore, by inactivating the fructokinase gene a 100% yield of mannitol from fructose is obtained.

The invention thus concerns a process for the production of mannitol by bioconversion, which process comprises the steps of bringing a high initial concentration of free, mannitol-producing lactic acid bacterial cells into contact with a low-nutrient medium supplemented with a substrate convertible into mannitol, and a cosubstrate, in a bioreactor system; performing the bioconversion under conditions suitable for converting said substrate into mannitol; separating the bacterial cells from the medium by filtration to obtain a cell-free solution; recovering from the cell-free solution the mannitol produced; and reusing the separated bacterial cells in the bioreactor system.

Consequently, an object of the present invention is to provide a semi-continuous or a continuous process for the production of mannitol. One process alternative to accomplish this is the re-use of free cell biomass in successive batch bioconversions as shown in FIG. 1. When the initial fructose is depleted the cells are concentrated e.g. by tangential flow filtration (TFF), whereby the mannitol is removed from the bioconversion reactor in the cell-free permeate. The cell concentrate is then diluted with fresh fructose-rich solution and a new batch is started. During the bioconversion the cells are kept in a resting or slowly growing state.

Another embodiment of the present invention provides a process where a fructose-rich solution in a mixing reactor is circulated through a bioconversion reactor containing free cells in a resting or slowly growing state. The cells are kept in the bioconversion reactor by cell-recycle techniques (e.g. TFF; see FIG. 2) and the cell-free permeate is re-circulated back to the mixing reactor. The volume in the bioconversion and mixing reactors is kept approximately constant.

A third embodiment of the present invention is a continuous process where a fructose-rich solution is added to a bioconversion reactor containing free cells in a resting or slowly growing state. The cells are kept in the bioconversion reactor by cell-recycle techniques (e.g. TFF) and the mannitol-rich, cell-free permeate is directed to downstream processing via a recovery tank (FIG. 3). The volume of the bioconversion reactor is kept constant by continuous stirred tank reactor (CSTR) techniques (e.g. by level controller, calibrated feed and harvest pumps, or balancing the bio conversion reactor).

Furthermore, the present invention relates to the use of LAB in the process. Several species can be used in the process with varying yields and productivities (see Table 1 in Example 9). For instance, *Leuconostoc pseudomesenteroides* has a high productivity, but a yield less than 80%. This is due to a strong leakage of fructose substrate to the phosphoketolase pathway via fructokinase-catalyzed phosphorylation. On the other hand, *Lactobacillus sanfranciscensis* gives a 100% mannitol yield from fructose, but is low in productivity (less than 0.5 g/L/h). To have both a high productivity and to maximize the yield, the fructokinase gene(s) is/are inactivated in the present invention in a high productivity species like *Leuconostoc mesenteroides*, *Leuconostoc pseudomesenteroides* or *Lactobacillus fermentum*.

Consequently, further objects of the invention are bacterial strains of the genus *Lactobacillus* or *Leuconostoc*, in which the fructokinase enzyme(s) is/are inactivated.

DETAILED DESCRIPTION OF THE INVENTION

Figure 1:
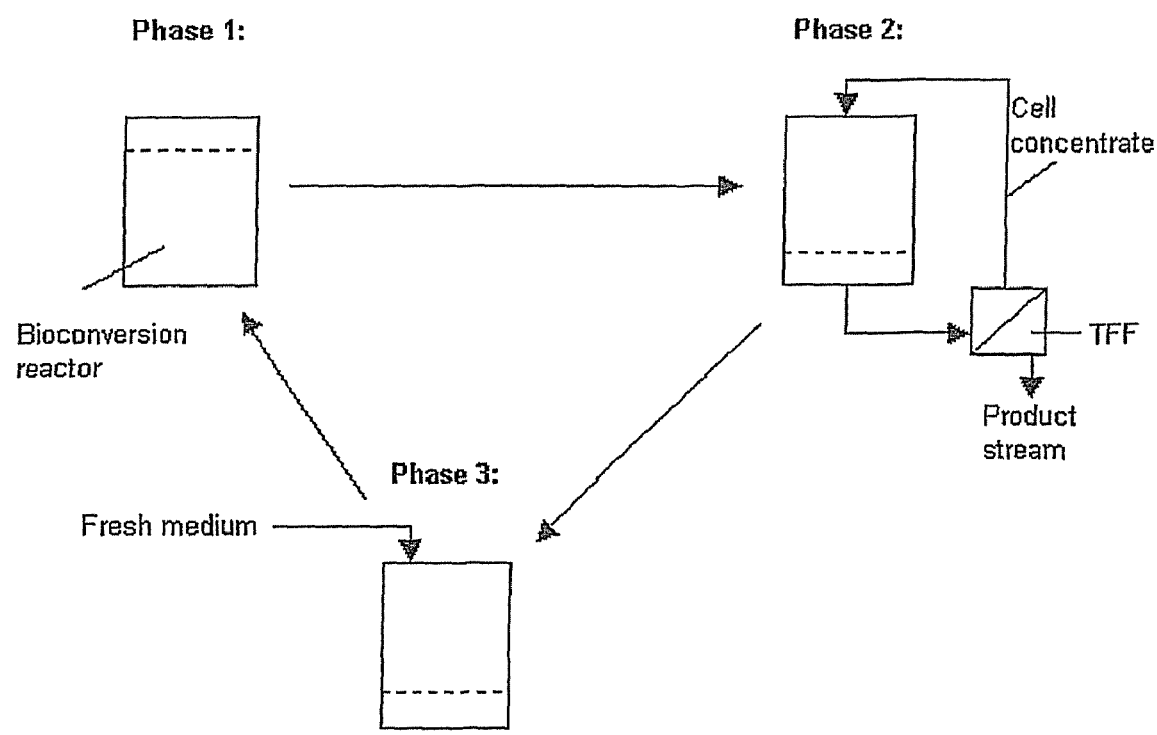
FIG. 1. Batch process alternative. Phase 1: Bioconversion. Phase 2: Product recovery and cell concentration with tangential flow filtration (TFF). Phase 3: Addition of fresh fructose-rich solution to the concentrated cell suspension.

The primary embodiment of the present invention is a process in which mannitol is produced by bioconversion from fructose with the aid of free native or fructokinase inactivated LAB cells kept in a resting or a slowly growing state. The volumetric mannitol productivities and mannitol yields from fructose for such a system are preferably above 10 g/L/h and 90 mole-%, respectively.

The preferred substrate for the bioconversion is fructose. Sucrose can be used as well. In addition, glucose is preferred as a co-substrate for the production of NAD(P)H, which is needed as a cofactor in the bioconversion of fructose into mannitol. Based on a 100 mole-% bioconversion yield of fructose into mannitol, the preferred molar ratio of fructose and glucose is 2:1. Typically among heterofermentative lactic acid bacteria a varying fraction of fructose that has been transported into the cells is phosphorylated by fructokinase-catalysis to form fructose-6-P and thus, channeled into the phosphoketolase pathway. The "leaking" fructose carbon skeleton is then converted stepwise into end products such as acetic and lactic acid, ethanol and carbon dioxide. When fructose is leaking to the phosphoketolase pathway and when the mannitol yield from fructose is less than 100 mole-%, it is preferable to increase the fructose to glucose ratio to avoid residual glucose concentrations. Preferred initial concentrations of fructose and glucose vary from 50 to 200 g/L and 20 to 100 g/L, respectively. The upper limit of initial fructose concentration is usually set by the maximum solubility of mannitol at the bioconversion conditions in question. An end concentration of mannitol over the maximum solubility would result in crystalline mannitol to form in the bioconversion reactor, which preferably should be avoided.

Instead of using high-purity fructose and/or glucose as the substrates, also respective compounds with a lower purity can be used as the substrate for the cells. This is preferred in order to lower the raw material costs, which are strongly influenced by the price of fructose and glucose. Besides the sugars noted earlier, the bioconversion medium also needs to be supplemented at least with complex nitrogen sources, magnesium and manganese ions. The preferred complex nitrogen sources are yeast extract, preferably in initial concentrations of 0.1 to 1 g/L, and tryptone, preferably in initial concentrations of 0.2 to 2 g/L. The concentrations of magnesium and manganese ions are preferably in the range from 0.1 to 0.5 g/L and 0.01 to 0.1 g/L, respectively. Concentrations providing optimum mannitol production depend on the strain in question and can therefore, deviate from the numbers shown above. The magnesium and manganese ions can preferably be added in the form of respective sulphates. Alternative and less expensive complex nitrogen sources are e.g. soybean and cottonseed meal, corn steep liquor (CSL), yeast hydrolysates etc.

The preferred minimum concentration of free cells in the bioconversion reactor is 5 g dry cell weight/L. A value over 10 g/L is preferred. The initial cell biomass production, which enables the first bioconversion cycle to proceed, can be achieved by cultivating the cells in a nutrient-rich growth medium, applying techniques such as batch, fed-batch, or CSTR cell-recycling. The cells are then concentrated to high cell densities, preferably 25 to 100 g dry cell weight/L, by e.g.

tangential flow filtration (TFF) or centrifugation. Once the cells are in the bio conversion reactor, in the preferred concentrations mentioned above, the same cells can be used for several successive batch bioconversions (see FIGS. 1 and 2). Hence, the processes according to alternatives shown in FIGS. 1 and 2 of the present invention are semi-continuous.

The bioconversion and the mixing reactors are preferably agitated vessels with the possibility to measure and control on-line the temperature and pH of the bioconversion medium. Pressure indicators should preferably also be available. The carbon dioxide formed during the bioconversion is preferably released via the headspace either in the bioconversion or in the mixing reactor or both. The vessels are preferably made out of food-grade stainless steel material and the system should preferably be suitable for aseptic process protocols. Several reactors may be used in series and/or in parallel. For instance, nitrogen flushing of the media can be used to improve the mannitol yields from fructose and the $CO_2$ removal from the bioreactors.

The temperature and pH of the bioconversion medium should preferably be controlled either in both the bioconversion and the mixing reactor or only in one of the reactors. The temperature can be adjusted either with e.g. water or steam, whereas the pH can be adjusted with e.g. NaOH, KOH, $NH_4$, OH, HCl or $H_2SO_4$ solutions. The temperature and pH should preferably be adjusted within the respective optimum values in order to provide maximum mannitol productivity.

A suitable microorganism, in its native form, should preferably express mannitol dehydrogenase activity and produce mannitol as its main metabolite. Among suitable microorganisms are *Leuconostoc mesenteroides, Leuconostoc pseudonzesenteroides, Lactobacillus brevis, Lactobacillus buchneri, Lactobacillus fermentum, Lactobacillus sanfranciscensis*, and *Oenococcus oeni*. The preferred species is *Leuconostoc mesenteroides* and especially strain ATCC-9135. The present invention is, however, not limited to these microorganisms. The present invention also refers to microorganisms with activities similar to those mentioned above. Also microorganisms derived, by e.g. recombinant techniques, from microorganisms mentioned above or from microorganisms with activities similar to those mentioned above, may be used in the process.

If the concentration of free cells in the bioconversion reactor is increasing too much so that e.g. the productivity is decreasing from a normal value, a suitable volume of the cell suspension can be removed from the system. In the batch version of the present invention (FIG. 1) this is preferably done before the fresh bio conversion medium is added to the high cell density suspension, in order to start a new batch-cycle. In the circulation version of the present invention (FIG. 2) the removal is preferably done while the mixing vessel is emptied after fructose depletion and then refilled with fresh bioconversion medium. In the continuous version of the present invention (FIG. 3) e.g. the dilution rate and the contents of the feeding solution are used to control the production of mannitol. If it is necessary to remove cells from the continuous bioconversion reactor, it can be done applying e.g. TFF techniques.

While a microfiltration membrane or a large ultrafiltration membrane (e.g. 1000 kDa) is used in the TFF equipment for cell separation, it is not expected that any other component would be concentrated to harmful levels in the system, while these are most likely removed from the bioconversion reactor with the permeate or alternatively consumed by the cells.

The inactivation of the fructokinase activity is accomplished either by classical mutagenesis or by targeted gene inactivation techniques. Classical mutagenesis is done by treating growing cells of LAB with 1-methyl-3-nitro-1-nitrosoguanidine and selecting for bacteria, which cannot grow on fructose as the sole carbon source. The obtained mutants are further tested for their ability to import fructose into the cell to assure that the growth defect on fructose is not caused by a mutation present in fructose permease. The fructose transport is verified using radioactively labeled fructose in the growth medium and detecting the radioactivity in separated washed cells. Alternatively, the transport of fructose can be indirectly confirmed by measuring the conversion of fructose to mannitol in growth medium containing fructose.

The targeted inactivation of the fructokinase gene is done either by disrupting or by deleting the fructokinase gene. The inactivation plasmids for both purposes are constructed using a vector plasmid with temperature sensitive replication origin, to enhance the integration event to the bacterial chromosome. One example of this kind of plasmid is pGhost4, which is a wide host-range plasmid, capable of replicating in many Gram-positive bacteria (Biswas et al., 1993). In the first phase the inactivation plasmid is transferred to LAB by electroporation and transformants are selected at a permissive temperature using antibiotic selection. In the second phase, integration of the plasmid to the bacterial chromosome is achieved by growing the transformants at a non-permissive temperature to plasmid replication, using still antibiotic selection.

In the disruption construct an internal fragment of the fructokinase gene is cloned to the vector plasmid and integration at the fructokinase locus will interrupt the coding sequence and thus prevent the formation of an active fructokinase enzyme. In the case of targeted deletion of the fructokinase gene, integration of the deletion plasmid in the second phase does not disrupt the coding sequence, but creates two regions of homologous sequences, which serve as excision sites in later steps. These regions determining the excision sites are cloned in the deletion plasmid in a consecutive order and all DNA sequences between these regions will be deleted when homologous recombination occurs. Also all plasmid sequences, together with the antibiotic resistance gene, will be removed from the bacterial chromosome. After integration of the deletion plasmid the transformant bacteria are grown without antibiotic and clones sensitive to antibiotic are selected and tested for growth on fructose. The clones that cannot grow on fructose as sole carbon source are selected. The conversion of fructose to mannitol will be determined, and also the growth on the same substrates, used for native LAB strains, will be tested.

Mannitol is the main bioconversion product of the present invention. Other bioconversion products, which are dissolved in the medium, are e.g. acetic and lactic acid, and ethanol. Most of the carbon dioxide in the liquid medium is preferably removed from the system as gaseous carbon dioxide through agitation and/or nitrogen flushing of the medium. The liquid product solution is separated from the cells by TFF, as shown in FIG. 1 (no additional cell separation step is needed in the other two process alternatives of the present invention). The rest of the product recovery process comprises of the following unit operations: concentration, crystallization, separation, drying, and homogenization. Alternatively also other metabolites formed, besides mannitol, can be recovered from the bio conversion medium.

The concentration of the liquid product solution is preferably done by evaporation. The heated concentrate is then transferred to a cooling crystallization unit, where mannitol crystals fall out when the temperature of the solution is decreased. Next the crystals are separated from the mother liquor by a drum separator and the crystals thereby collected (crystals A). The mother liquor is either added to the next recovery cycle or re-crystallized separately (crystals B). Alternatively, the mother liquid, if containing residual fructose, can be recycled back to the bioconversion step. The crude crystals (A and B) are dissolved in hot water, whereafter the solution is re-crystallized in a cooling crystallization unit. After a second drum separation step the white crystals are dried in a vacuum or under-pressure oven. Finally, if needed, the dry crystals are homogenized by a suitable method. According to the protocol presented above the total mannitol recovery yield and crystal purity achieved, is preferably 50 to 100 mass-%, and 95 to 100 mass-%, respectively.

Example 1

Production of Cells for the Bioconversion Phases 1

A bench-top bioreactor containing 9.7 L of nutrient-rich fermentation medium (Soetaert et al., 1999) was inoculated with 300 mL of a 16-h cell culture of *Leuconostoc pseudomesenteroides* ATCC-12291 grown in an inoculation medium (Soetaert et al., 1999). The temperature of the growth medium (10 L) was set first at 20° C. and after 56 h raised to 25° C. The pH was controlled at 5.0. The solution was slowly agitated.

After about 66 hours the cultivation was stopped and the cells recovered by tangential flow filtration (Pellicon® 2 Mini Holder and Biomax® 1000 (V screen) membrane, Millipore Corp., USA). From an initial volume of 10.9 L (~3 g dry cell weight/L) a 0.7-L cell concentrate (~47 g dry cell weight/L) was obtained by this filtration technique. The cell-free permeate (10.2 L) could thereafter be used for study of mannitol recovery. The cell concentrate can be used as the initial biomass for the processes described in Examples 3-5.

The volumetric mannitol productivity of this free cell process was 1.7 g/L/h.

Example 2

Production of Cells for the Bioconversion Phases 2

A bench-top bioreactor containing 1.9 L of MRS growth medium (40 g/L glucose) was inoculated with 100 mL of a 10-h cell culture of *Leuconostoc mesenteroides* ATCC-9135 also grown in a MRS growth medium (30 g/L glucose). The temperature and pH of the growth medium (2 L) were set at 30° C. and 6.0, respectively. The solution was slowly agitated.

About 9.5 hours later the cells were harvested by centrifugation. The cell pellet was then suspended in a fresh bioconversion medium (See Examples 3-5).

Example 3

Production of Mannitol by Bioconversion in a Batch Mode (FIG. 1)

The cell pellets obtained in Example 2 was suspended with fresh bioconversion medium and transferred aseptically into a bioconversion reactor. The total volume of the solution was 425 mL and it had the following initial composition: 100 g/L fructose, 50 g/L glucose, 1 g/L tryptone, 0.5 g/L yeast extract, 2.62 g/L $K_2HPO_4.3H_2O$, 0.2 g/L $MgSO_4$, and 0.01 g/L $MnSO_4$. The cell concentration during the bioconversion was approximately 10 g dry cell weight/L.

The temperature control was set at 30° C. and the pH was controlled at 5.0 with 3 M NaOH. The solution was slowly agitated.

After 4.5 hours of bioconversion time the cells had consumed all of the sugars and the experiment was ended. The average volumetric mannitol productivity for the process was 20.7 g/L/h. The mannitol yield from fructose was 91.2 mole-%.

Furthermore, the product solution and cells can be separated by e.g. TFF, and the cell concentrate re-used in successive batch bioconversions according to the process description in FIG. 1.

Example 4

Figure 2:
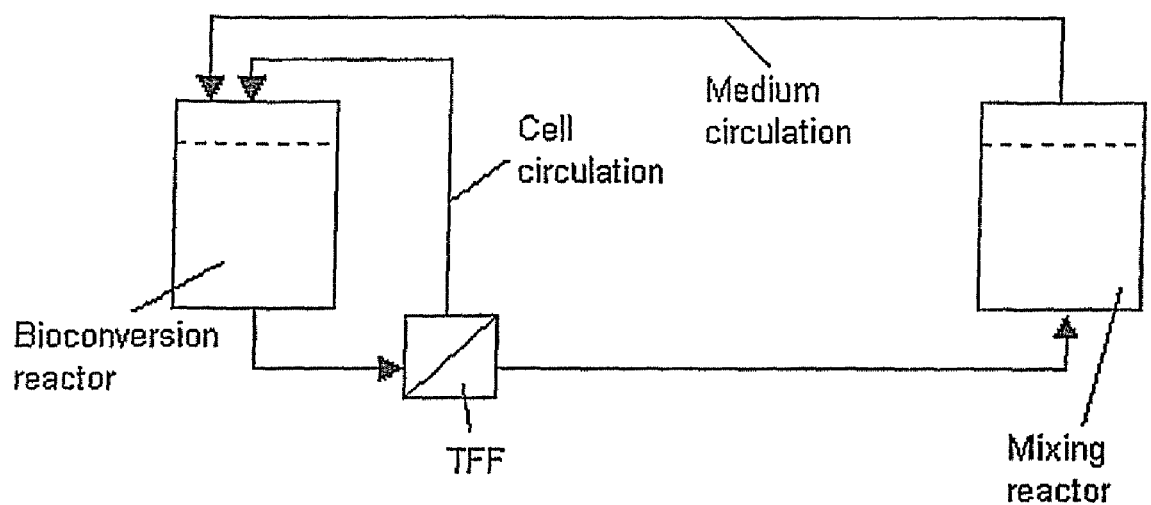
FIG. 2. Circulation process alternative. The cells are kept within the system consisting of the bioconversion reactor unit, the retentate side of the filtration unit and the circulation loop. Fructose-containing solution is pumped from the mixing reactor at the same flow rate as permeate is added to the mixing reactor.

Production of Mannitol by Bioconversion with Circulation (FIG. 2)

The experiment set up is shown in FIG. 2. The cell pellets, obtained as described in Example 2, were, suspended in fresh bioconversion medium lacking the sugars and transferred aseptically to the bioconversion reactor unit. The volume in the bioconversion reactor unit was 0.4 L. A TFF unit (Pellicon® 2 Mini Holder and Biomax® 1000 (V screen) membrane, Millipore Corp., USA) was attached to the bioconversion bioreactor unit and the permeate flow was lead to a mixing reactor. The mixing reactor (volume 1.0 L) was standing on a balance and the mass of the reactor was kept constant by circulating medium back to the bioconversion reactor unit. The total volume of the whole system was 1.5 L and the medium had the following initial composition: 100 g/L fructose, 50 g/L glucose, 1 g/L tryptone, 0.5 g/L yeast extract, 2.62 g/L $K_2HPO_4.3H_2O$, 0.2 g/L $MgSO_4$, and 0.01 g/L $MnSO_4$. The cell concentration in the bioconversion reactor was 8.7 g dry cell weight/L.

The temperature and the pH were controlled both in the bioconversion reactor and in the mixing reactor units. The temperature control was set at 30° C. and the pH was controlled at 5.0 with 3 M NaOH. Mixing was applied in both reactors.

After 9 hours of bioconversion time the cells had consumed all of the sugars and the experiment was ended. The average volumetric mannitol productivity for the process was 21.6 g/L/h. The mannitol yield from fructose was 94.0 mole-%.

Example 5

Figure 3:
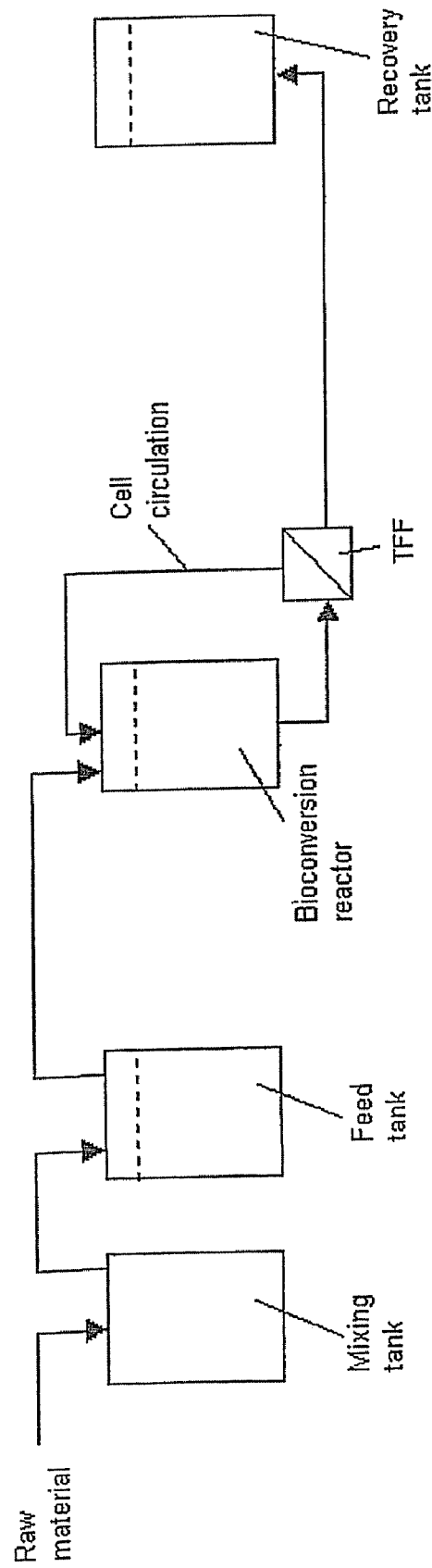
FIG. 3. Continuous process alternative. Fresh fructose-rich solution is prepared in the mixing reactor, which is then transferred into the feed tank. Solution is added to and removed from the bioconversion reactor system, consisting of the bioconversion reactor unit, the retentate side of the filtration unit and the circulation loop, at the same flow rates.

Production of Mannitol by Bioconversion in a Continuous Reactor (FIG. 3)

The experiment set up is shown in FIG. 3. The cell pellets, obtained as described in Example 2, were suspended in fresh bioconversion medium lacking the sugars and transferred aseptically to the bioconversion reactor unit. A TFF unit (Pellicon® 2 Mini Holder and Biomax® 1000 (V screen) membrane, Millipore Corp., USA) was attached to the bioconversion bioreactor unit and the permeate flow was lead to a recovery tank. The total volume in the bioconversion reactor unit, retentate side of the filtration unit, and in the circulation loop was 1.0 L. The bioconversion reactor unit was standing on a balance and the mass of the reactor was kept constant by adding fresh medium from a feed tank. The feeding solution following initial composition: 25 g/L fructose, 12.5 g/L glucose, 1 g/L tryptone, 0.5 g/L yeast extract, 2.62 g/L $K_2HPO_4.3H_2O$, 0.2 g/L $MgSO_4$, and 0.01 g/L $MnSO_4$. The cell concentration in the bioconversion reactor, at dilution rate 0.68 l/h, was approximately 6.9 g dry cell weight/L.

The temperature control was set at 30° C. and the pH was controlled at 5.0 with 3 M NaOH. The reactor was slowly agitated. A volumetric mannitol productivity of 12.5 g/L/h was achieved. The mannitol yield from fructose was 93.0 mole-%.

Example 6

Inactivation of the Gene Encoding Fructokinase by Random Mutagenesis

Chemical mutagenesis of *L. pseudomesenteroides* ATCC-12291 was done using log-phase cells ($OD_{600}$ 1.0) grown in M17 supplemented with 1% glucose (GM17). Cells washed with 50 mM sodium phosphate buffer, pH 7, were treated with 1-methyl-3-nitro-1-nitrosoguanidine, 0.5 mg/ml, for 40-50 min, at room temperature, and washed three times with the buffer above. Washed cells were incubated in GM17, for 1 hour, at 30° C., and plated on GM17 agarose, incubated 2 days at 30° C. Colonies on GM17 plates were replica-plated on a chemically defined medium (CDM; Anon., 2000) supplemented with either 1% glucose or 1% fructose. After 2 days of incubation at 30° C. colonies growing on glucose, but not on fructose, were selected. Conversion of fructose to mannitol will indicate that the fructose permease is not affected by the mutagen. The fructokinase inactivated production strain, which was able to convert fructose to mannitol, was named BPT-143. The strain was deposited according to the Budapest Treaty at the Deutsche Sammlung von Mikroorganismen und Zellkulturen, GmbH, Mascheroder Weg 1b, D-34124 Braunschweig, Germany on 13 Nov. 2001 with the accession number DSM 14613.

Example 7

Inactivation of the Gene Encoding Fructokinase by Directed Mutagenesis

Inactivation plasmid for disrupting the fructokinase gene(s) of *Lb. fermentum* is constructed by joining an internal fragment of a fructokinase gene between suitable restriction sites of pGhost4. The ligation mixture is electroporated to *Lactococcus lactis*, transformants are incubated for 1 day, at permissive temperature, 30° C., using erythromycin (Em, 5 µg/ml) and screened by PCR with pGhost4-specific primers. Recombinant plasmids, containing the internal fragment of fructokinase gene, are isolated and electroporated to *Lb. fermentum*. Transformants are incubated anaerobically, for 1 day, at 30° C., and verified by PCR with the previously mentioned primers. Clones carrying the recombinant plasmids selected for the integration experiments are grown over night, at 30° C., in MRS growth medium supplemented with 5 µg/ml Em. These cell suspensions are used as inoculate for new cultures grown for 5 hours at 42° C. in same medium. Then the cell suspensions are diluted 1:100 000, plated on MRS-Em, and incubated for 2 days at 42° C. Colonies arising in the presence of Em at 42° C. will have a disruption plasmid integrated to the chromosome at the fructokinase locus. Disruption of the fructokinase gene(s) will result in reduced fructokinase activity of the disruption transformants compared to the wild type *Lb. fermentum* grown in MRS or CDM supplemented with different sugars (sucrose, fructose, lactulose, maltose, galactose or ribose) and 5 µg/ml Em. Disruption of the fructokinase gene(s) is confirmed by Southern blotting of the chromosomal DNA isolated from the clones with reduced fructokinase activity.

Fructokinase genes are deleted using the following protocol. Two 0.5 kb fragments amplified by PCR from *Lb. fermentum* chromosome, surrounding the targeted deletion site, are ligated to pGhost4. The ligation mixture is electroporated to *L. lactis*, transformants are incubated for 1 day at permissive temperature, 30° C., using erythro-mycin (Em, 5 µg/ml) and screened by PCR with pGhost4-specific primers. Plasmids containing the cloned fragments are isolated and electroporated to *Lb. fermentum*. Transformants are incubated anaerobically on MRS-Em plates for 1 day at 30° C. and resulting colonies are verified by pGhost4-specific primers to ensure the presence of the recombinant plasmids and correct insert sizes. Raising the temperature as described for the disruption plasmids will result in integration of the recombinant plasmid to the chromosome. Sites of the integration are confirmed by Southern blotting of chromosomal DNA isolated from the integrant strains. The *Lb. fermentum* carrying an integrated recombinant plasmid at a fructokinase locus is then grown without Em, at 42° C., for 100 generations and plated on MRS without Em. Omission of the antibiotic will result in dissociation of the integrated plasmid from the chromosome. Depending on the recombination site either restoration of the wild type or deletion of a fructokinase gene will happen. In both cases all foreign DNA will be removed from the chromosome. Em-sensitive clones are detected after replica plating on MRS with and without Em. Among the Em-sensitive clones those with reduced fructokinase activity are selected. Deletion of the fructokinase gene is confirmed by Southern blotting the chromosomal DNA isolated from the deletion strains.

Example 8

Production of Mannitol by *L. pseudomesenteroides* with Inactivated Fructokinase Gene (Random Mutagenesis)

*L. pseudomesenteroides* ATCC-12291 and the clone DSM 14613 (BPT 143) with in-activated fructokinase gene (see Example 6) were tested for mannitol production in parallel experiments. The growth medium had the following composition: 20 g/L fructose, 10 g/L glucose, 10 g/L tryptone, 5 g/L yeast extract, 2.62 g/L $K_2HPO_4.3H_2O$, 0.4 g/L $MgSO_4$, and 0.02 g/L $MnSO_4$. The temperature and pH was set at 30° C. and 5.0, respectively. The bioconversion time was 8 hours. The mannitol yields from fructose for the native strain and the clone were 73.7 mole-% and 85.7 mole-%, respectively. Also, a 25% improvement in volumetric mannitol productivity was observed.

Example 9

Comparison of Mannitol Production Capacity of Lactic Acid Bacteria in a Resting or Slow-Growing State Pre-cultures of three of the most promising strains (preliminary comparison studies not shown) were grown in MRS growth medium. The cell suspensions were centrifuged and the cell pellets washed in 0.2 M phosphate buffer (pH 5.8). After an additional centrifugation separation the cell pellets were resuspended in the same buffer. The concentrated cell suspensions (50 mL per strain) were added to bioreactors containing 450 mL of a bioconversion medium. After addition the composition of the solution was the following: 20 g/L fructose, 10 g/L glucose, 0.5 g/L tryptone, 0.25 g/L yeast extract, 2.62 g/L $K_2HPO_4.3H_2O$, 0.2 g/L $MgSO_4$, and 0.01 g/L $MnSO_4$.

The temperature and pH of the bioconversion medium were set at 30° C. and 5.0, respectively. The bioconversion media were slowly agitated. The key results are shown in Table 1.

TABLE 1

The volumetric mannitol productivities ($r_{mtol}$) and mannitol yields from glucose ($Y_{mtol/fru}$) after 8 hours of bioconversion time.

| Strain: | $r_{mtol}$ (g/L/h) | $Y_{mtol/fru}$ (mole/mole) |
|---|---|---|
| Leuconostoc mesenteroides ATCC-9135 | 2.3 | 97.8 |
| Leuconostoc pseudomesenteroides ATCC-12291 | 1.5 | 79.6 |
| Lactobacillus fermentum NRRL-1932 | 1.0 | 86.1 |

Example 10

Recovery of Mannitol

The cell-free permeate, described in Example 1, was concentrated to approximately 250 g mannitol/L by evaporating with a Rotavapor unit. The concentrate (T=35° C.) was transferred into a cooling crystallization unit and the temperature was linearly (15 h) decreased to 5° C. The solution was slowly agitated. The crystals were separated by filtration and the mother liquor was re-crystallized as described above.

The wet crystals from the first and the second cycle were combined and dissolved in distilled water (T=45° C.). The mannitol concentration of the solution was approximately 300 g/L. The solution was transferred into a cooling crystallization unit and the temperature was linearly (15 h) decreased to 5° C. The crystals were separated by filtration and finally, the wet crystals were dried overnight at 60° C.

The recovery yield was about 55 mass-% and the purity above 99.5 mass-%. The mannitol found in the washing solution gained from the last crystallization step can be re-used as part of the washing solution in the next recovery cycle. Adding this hypothetical amount of mannitol to the crystals obtained in the first recovery cycle a final recovery yield of about 71% was achieved.

Deposited Microorganisms

The following microorganism was deposited according to the Budapest Treaty at the Deutsche Sammlung von Mikroorgmismen und Zellkulturen, GmbH, Mascheroder Weg 1b, D-34124 Braunschweig, Germany.

| Microorganism | Accession number | Deposit date |
|---|---|---|
| Leuconostoc pseudomesenteroides BPT-143 | DSM 14613 | 13 Nov. 2001 |

REFERENCES

Anonymous (2000) CDM (Chemical Defined Medium). http://www.biol.rug.nl/lacto/protocols/medium_cdm_lab.html 25.1.2000

Axelsson, L T (1993) Lactic acid bacteria: Classification and Physiology. In: Salminen S, von Wright A (eds) Lactic acid bacteria, Marcel Dekker Inc, New York, pp 1-64

Biswas I, Gruss A, Ehrlich D, Maguin E (1993) High-efficiency gene inactivation and replacement system for gram-positive bacteria. J Bacteriol 175: 3628-3635

Bär A (1985) Safety assessment of polyol sweeteners—some aspects of toxicity. Food Chem 16: 231-241

Erten H (1998) Metabolism of fructose as an electron acceptor by Leuconostoc mesenteroides. Proc Biochem 33: 735-739

Hideyuki S, Hachiro O, Koji K. (1987) Production of mannitol. Patent JP 622 399 95

Ikawa T T, Watanabe T, Nisizawa K (1972) Enzyme involved in the last steps of biosynthesis of mannitol in brown algae. Plant Cell Physiol 13: 1017-1027

Itoh Y, Tanaka A, Araya H, Ogasawara K, Inabi H, Sakamoto Y, Koga J (1992) Lactobacillus B001 for manufacture of mannitol, acetic acid, and lactic acid. Patent EP 486 024

Itoh Y, Tanaka A, Araya H (1995) Method for separating and purifying mannitol. Patent EP 683 152

Korakli M, Schwarz E, Wolf G, Hammes W P (2000) Production of mannitol by Lactobacillus sanfranciscensis. Adv Food Sci 22: 1-4

Ojamo H, Koivikko H, Heikkilä H (2000) Process for the production of mannitol by immobilized micro-organisms. Patent application WO 00/04181.

Pilone G J, Clayton M G, van Duivenboden R J (1991) Characterization of wine lactic acid bacteria: single broth culture for tests of heterofermentation, mannitol from fructose, and ammonia from arginine. Am. J Enol Vitic 42 153-157

Perry R H, Green, D W, Maloney, J O (1997) Perry's Chemical Engineers' Handbook. 7th ed. McGraw-Hill, New York, p 2-40

Pimentel M S, Silva M H, Cortês I, Faia A M (1994) Growth and metabolism of sugar and acids of Leuconostoc oenos under different conditions of temperature and pH. J Appl Bacteriol 76: 42-48

Salou P, Loubiere P, Pareilleux A (1994) Growth and energetics of Leuconostoc oenos during cometabolism of glucose with citrate or fructose. Appl Environ Microbiol 60: 1459-1466

Soetaert W, Buchholz K, Vandamme E J (1994) Production of D-mannitol and D-lactic acid from starch hydrolysates by fermentation with Leuconostoc mesenteroides. CR Acad Agric Fr 80: 119-126

Soetaert W, Vanhooren P T, Vandamme E J (1999) The production of mannitol by fermentation. Methods Biotechnol 10 (Carbohydrate Biotechnology Protocols): 261-275

Takemura M, Iijima M, Tateno Y, Osada Y, Maruyama H (1978) Process for preparing D-mannitol. U.S. Pat. No. 4,083,881.

The invention claimed is:

1. A process for the production of mannitol by bioconversion, comprising the steps of
    bringing an initial concentration of at least 5 g dry cell weight per liter of free, mannitol-producing fructokinase-inactivated lactic acid bacterial cells into contact with a nutrient medium supplemented with a substrate convertible into mannitol, and a cosubstrate, in a bioreactor system,
    performing the bioconversion under conditions suitable for converting said substrate into mannitol including keeping the cells in a resting or a slow growing state such that the average volumetric productivity of mannitol is at least 10 g/L/h,
    separating the bacterial cells from the medium by filtration to obtain a cell-free solution,
    recovering from the cell-free solution the mannitol produced, and
    reusing the separated bacterial cells in the bioreactor system.

2. The process according to claim 1, wherein the bacterial cells are native lactic acid bacterial cells.

3. The process according to claim 2, wherein the bacterial cells are of the strain Leuconostoc mesenteroides ATCC-9135.

4. The process according to claim 1, wherein the bacterial cells are of the strain *Leuconostoc pseudomesenteroides* BPT143 deposited under accession number DSM 14613 at the Deutsche Sammlung von Mikroorganismen and Zellkulturen GmbH.

5. The process according to claim 1, wherein the substrate is fructose.

6. The process according to claim 1, wherein the cosubstrate is glucose.

7. The process according to claim 1, wherein the bioconversion is performed until at least 70% of said substrate has been consumed.

8. The process according to claim 1, wherein the bioconversion is performed as a batch process in a bioreactor system comprising a bioconversion reactor unit and a filtration unit.

9. The process according to claim 1, wherein the bioconversion is performed as a circulation process in a bioreactor system comprising a bioconversion reactor unit, a filtration unit and a mixing reactor unit.

10. The process according to claim 9, wherein the bacterial cells are circulated between the bioconversion reactor unit and the filtration unit.

11. The process according to claim 9, comprising the steps of leading the cell-free solution obtained by the filtration into the mixing reactor, and transferring the solution from the mixing reactor back to the bioconversion reactor unit.

12. The process according to claim 9, comprising emptying the mixing reactor unit after the bioconversion step, and re-filling it with said nutrient medium supplemented with said substrate and co-substrate, to run successive bioconversions reusing the bacterial cells.

13. The process according to claim 9, wherein said bioconversion is run in two or more bioconversion reactor units in series or in parallel.

14. The process according to claim 1, wherein the bioconversion is performed as a continuous process in a bioreactor system comprising a mixing tank, a feed tank, a bioconversion reactor unit, a filtration unit and a recovery tank.

15. The process according to claim 14, wherein the bacterial cells are circulated between the bioconversion reactor unit and the filtration unit.

16. The process according to claim 14, comprising the steps of feeding the bioconversion reactor unit continuously with said nutrient medium supplemented with said substrate and co-substrate, and removing the cell-free solution gained by filtration from the bioreactor system to withhold a constant volume in the bioconversion reactor unit.

* * * * *